United States Patent [19]
Zyhowski et al.

[11] Patent Number: 5,610,128
[45] Date of Patent: Mar. 11, 1997

[54] SURFACTANTS AND DRYING AND DRYCLEANING COMPOSITIONS WHICH UTILIZE SAID SURFACTANTS

[75] Inventors: Gary J. Zyhowski; David Nalewajek; Leonard M. Stachura, all of Erie, N.Y.

[73] Assignee: AlliedSignal Inc., Morris Township, N.J.

[21] Appl. No.: 355,587

[22] Filed: Dec. 14, 1994

[51] Int. Cl.$^6$ ................................ C11D 1/34; C11D 1/62
[52] U.S. Cl. ........................ 510/288; 510/285; 987/217
[58] Field of Search ................................. 252/544, 547, 252/548; 260/924; 510/285, 288

[56] References Cited

U.S. PATENT DOCUMENTS

| | | | |
|---|---|---|---|
| 3,386,181 | 6/1968 | Steinacker | 34/9 |
| 4,147,743 | 4/1979 | Bathelt et al. | 260/924 |
| 4,618,447 | 10/1986 | Seelig | 252/139 |
| 4,655,958 | 4/1987 | Jung et al. | 252/194 |
| 5,102,469 | 4/1992 | Buchwald et al. | 134/22.14 |
| 5,125,978 | 6/1992 | Flynn et al. | 134/2 |

FOREIGN PATENT DOCUMENTS

| | | |
|---|---|---|
| 3-213595 | 9/1991 | Japan . |
| 1269095 | 3/1972 | United Kingdom . |

OTHER PUBLICATIONS

Haywood, L., Et Al "Amine (Polyfluoroalkoxyacyl) Imide Surfactamts", Journal of Fluorine Chemistry, 51 (1991) 419–431.

*Primary Examiner*—Paul Lieberman
*Assistant Examiner*—Necholus Ogden
*Attorney, Agent, or Firm*—Colleen D. Szuch

[57] ABSTRACT

Novel surfactants and drying, drycleaning and soil repellency compositions containing such surfactants which utilize such surfactants. The surfactants are fluorine containing quaternary ammonium salts, and the drying, drycleaning and soil repellency compositions contain at least one halocarbon component and at least one of the fluorine containing surfactants. These compositions have the ability to remove water or aqueous films from the surfaces of a broad range of substrates and impart soil repellency to fabrics.

27 Claims, No Drawings

SURFACTANTS AND DRYING AND DRYCLEANING COMPOSITIONS WHICH UTILIZE SAID SURFACTANTS

BACKGROUND OF THE INVENTION

1. Field of the Invention

The invention relates to novel surfactants and drying, drycleaning and soil repellency compositions which utilize such surfactants. More particularly, the invention relates to fluorine containing surfactants, and drying, drycleaning and soil repellency compositions which contain at least one halocarbon solvent component and at least one fluorine containing surfactant. Such compositions have the ability to remove water or aqueous films from the surfaces of a broad range of substrates and impart soil repellency to fabrics.

2. Description of the Prior Art

Many industries use aqueous compositions for the surface treatment of metals, ceramics, glass, and plastics. Cleaning, plating, and deposition of coatings is often carried out in aqueous media but must be followed by a drying step. Hot air drying, centrifugal drying, and solvent-based water displacement are among the methods used. While hot air drying is commonly used to remove water from the work, the high energy requirement to heat air results in a significant expense. A variety of solvent-surfactant drying compositions for water displacement are also well known to those skilled in the art. The advent of certain hydrofluorocarbons (HFC's) allows the industry to utilize vapor degreasing and its advantages of low energy requirements, flash drying, recyclability, and high throughput. Drying compositions based on trichloroethylene or chlorofluorocarbon-113 have been used. However, concerns due to toxicity and environmental acceptability have led to a decline in the use of such systems.

HFC solvent containing drying compositions are known in the art. Illustrative of such compositions are those described in U.S. Pat. Nos. 4,438,026 and 4,401,584 which are incorporated herein by reference. These compositions remove water from a substrate by displacement. Many HFC's have the disadvantage of limited solvency for hydrocarbon oils and fluxes and the use of surfactants is important in many applications. Halocarbons and a properly selected hydrophobic surfactant can be used to displace water from water laden work. However, the identification of the appropriate surfactants to accomplish water displacement is not trivial. Drycleaning and drying or water displacement require surfactants that impart distinct properties to solvent mixtures. For removing oils from machined metal parts, a surfactant aids in removal of soils that would otherwise be only sparingly soluble in a hydrofluorocarbons. Water displacement requires a surfactant that does not form a stable emulsion with water.

In addition, just as many hydrofluorocarbons are unable to dissolve many soils, they are unable to dissolve a number of surfactants. Therefore, one must not only identify those surfactants which are soluble in the HFC, but also those having the desired activity in the HFC. Furthermore, there are differences among the classes of surfactants, e.g., anionic versus cationic, among surfactants within a class, e.g., the presence or absence of a sulfide linkage, and even among similar surfactants that only differ in chain length. It has been a problem in the art to find a hydrophobic surfactant that is essentially insoluble in water, will not form an emulsion with water and yet is still able to displace water from a variety of surfaces.

It has now been found that by the use of the inventive surfactant, the performance of HFC's in drying, drycleaning and soil repellency composition is enhanced. The invention has found a new class of HFC soluble hydrophobic fluorosurfactants with surface activity in the HFC that is useful to displace water. More particularly, the composition of this invention comprises one or more organic halocarbons and an effective amount of one or more fluorine containing quaternary ammonium salts.

The solvent drying composition of the invention is very effective in displacing water from a broad range of substrates including metals, such as stainless steel, aluminum alloys, brass and the like; and from glass and ceramic surfaces, such as glass, borosilicate glass, unglazed alumina, silica such as silicon wafers used in miniaturized electronic circuits, fired alumina and the like. The compositions of the invention do not form noticeable emulsions with the displaced water or form insignificant amounts of such emulsion.

In another embodiment of the invention, there is provided a novel surfactant-solvent composition and a process for treating fabric to impart soil repellency. The surfactant-solvent composition promotes soil removal, and when present in a rinse stage imparts oil repellency. It is an important feature of this invention that the surfactant contain at least one aromatic substituent in a cationic quaternary ammonium moiety. Because of the presence of the fluorinated substituent or substituents, these materials are soluble in the halocarbon, thus forming substantially homogeneous compositions, and can displace water from a broad range of substrates and aid in the removal of soils from fabric.

DESCRIPTION OF THE INVENTION

We have found that the placement of fluorine on the surfactant molecule is critical to surfactant solubility in hydrofluorocarbons while still maintaining surface activity and hydrophobicity of the surfactant. We have discovered that simply having fluorine in a surfactant structure is not enough. It is important to use a surfactant of structure (I) or (II). Prior art and commercially available fluorine containing surfactants are not soluble in HFC's or fail to impart adequate surface activity for drying with HFC's.

The invention comprises in part, a surfactant of the formulae:

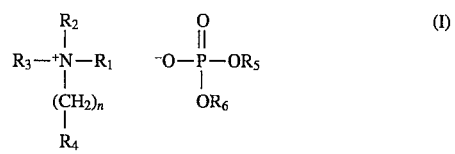

or

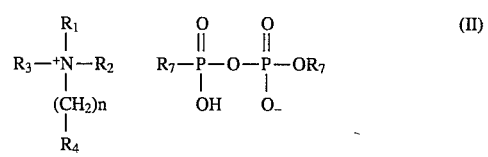

wherein $R_1$, $R_2$, $R_3$ can be the same or different and are linear or branched $C_1$ to $C_{16}$ alkyl, fluoroalkyl, alkylaryl or

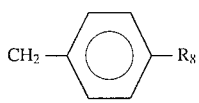

where
- $R_8$ is hydrogen or a linear or branched $C_1$ to $C_{16}$ alkyl or fluoroalkyl group;
- $R_4$ is $C_1$ to $C_{18}$ perfluoroalkyl;
- $n$ is from 1 to 4;
- $R_5$, $R_6$ and $R_7$ can be the same or different and are H, linear or branched $C_1$ to $C_{16}$ alkyl, fluoroalkyl or alkylaryl group or

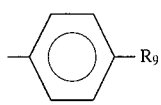

where $R_9$ is a linear or branched a $C_1$ to $C_{16}$ alkyl or fluoroalkyl group provided not more than one of $R_5$, $R_6$ and $R_7$ is H, and mixtures of such surfactants. Especially useful aromatic surfactants for use in the practice of this invention are the dimethylbenzyl 1,1,2,2 tetrahydroperfluorodecylamine salt of 4-tert-octylphenyl (mono- and di-) acid phosphate; and diethylmethyl 1,1,2,2 tetrahydroperfluorodecylamine salt of 4-tert-octyl(mono- and di-) acid phosphate. The examples illustrate methods of synthesizing and using these surfactants.

The invention is also directed to a composition comprising effective amounts of a halocarbon and a surfactant of the formulae:

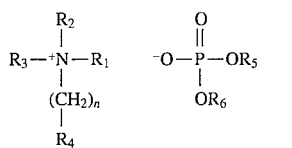

or

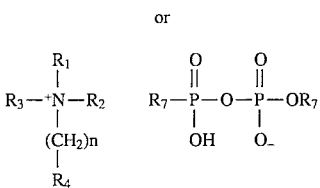

wherein $R_1$ through $R_7$ are as defined above, and wherein the halocarbon and surfactant are present in an amount sufficient to provide an effective drying, drycleaning or soil repellency composition.

The primary function of the halocarbon is to reduce the amount of water on the surface of the article to be dried. The primary function of the surfactant is to assist in cleaning the article and to displace any remaining water from the surface of the article. When the components are combined, an effective drying, drycleaning and soil repellency composition is attained. As used herein an effective amount of the surfactant is any amount which is capable of improving the drying, drycleaning or soil repellency capability of the halocarbons to any extent. It is that amount which when added to the halocarbon produces an effective drying, drycleaning or soil repellency composition.

The preferred embodiment of the fluorine containing surfactant may be prepared according to the following scheme. Other compounds within the above surfactant class may be prepared analogously. For those surfactants not specifically shown, modifications to this scheme for the manufacture others would be readily apparent to one skilled in the art.

Step 1:

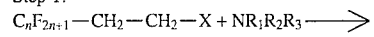

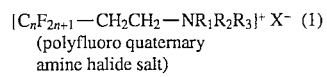
(polyfluoro quaternary amine halide salt)

where X is halogen and $R_1R_2R_3$ are defined above.

Step 2:
octylphenol + $P_2O_5 \longrightarrow$ octylphenylacid phosphate

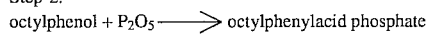

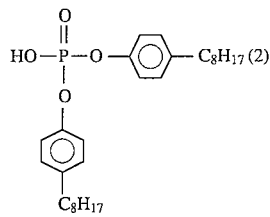

Step 3
octylphenylacid phospahte + triethylamine $\longrightarrow$ triethylamine salt of octylphenylacid phosphate $(2) + (C_2H_5)_3N \longrightarrow$

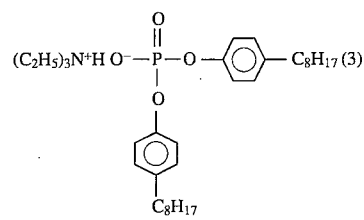

Step 4
Exchange polyfluoro quaternary amine for the triethylamine of the octylphenylacid phosphate.

$(1) + (3) \longrightarrow$

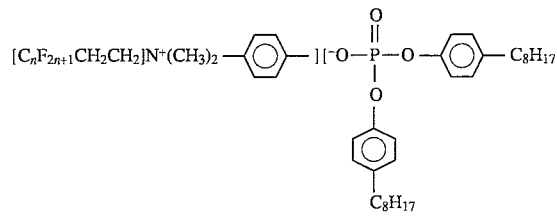

The halocarbon can be linear or branched, aliphatic, aromatic, cyclic, or contain a heteroatom, e.g. oxygen, nitrogen or sulfur. The halocarbon may also be aromatic, e.g. parachlorobenzotrifluoride, orthochlorobenzentrifluoride, 3,4-dichlorobenzotrifluoride or benzotrifluoride. Preferably the halocarbon component can be at least one volatile halocarbon. For purposes of this invention, a volatile halocarbon is a halocarbon having a boiling point of at least about 20° C. at atmospheric pressure. Preferred volatile halocarbons are halocarbons having a boiling point of at least 28° C. at atmospheric pressure, and particularly preferred volatile halocarbons are chloro and/or fluoro substituted alkanes. Among these particularly preferred volatile halocarbons, hydrofluorocarbons, methylene chloride, trichloroethylene, and perchloroethylene are more preferred and 1,1,1,2,2,4-hexafluorobutane, or HFC-356mcf is most preferred. Many HFC's useful for this invention are available commercially and others may be prepared according to any of the methods known in the art. HFC 356mcfq is currently not commercially available. It may be prepared according to the method of Example 6. Other methods are apparent to those skilled in the art.

The amounts of halocarbon and surfactant included in the composition of the invention can vary widely depending on the application, e.g. drying, drycleaning and soil repellency in which said composition will be used, but are readily apparent to those skilled in the art. U.S. Pat. Nos. 4,438,026 and 4,401,584, which are incorporated herein by reference, disclose the proportions in which such materials are combined.

Generally, the amount of such a surfactant is not greater than about 5 weight percent based on the total weight of the composition. However, while not economical, larger amounts can be used if after treatment with the composition the article being dried is thereafter treated with a volatile halocarbon having either no surfactant or small amounts.

In the preferred embodiment of the invention, for drying applications, the amount of surfactant is at least about 50 parts per million, preferably from about 50 to about 5000 ppm and most preferably from about 100 to about 2000 ppm based on the weight of the composition. For drycleaning applications, surfactant concentration may range from about 0.005 to about 3.0 wt. % and preferably from about 0.01 to about 0.5 wt. % based on the weight of the composition.

The composition of this invention can be used to clean and/or dry nonabsorbent articles constructed of such material as metals, glasses, ceramics and the like. In this regard, the invention provides a method for drying the surface of a substrate which comprises contacting or exposing the substrate with a composition comprising effective amounts of a halocarbon and a surfactant of the formulae (I) or (II) above, and then removing the composition from the substrate, for example by evaporation.

The invention provides a method for drycleaning an article which comprises contacting or exposing the article with a composition comprising effective amounts of a halocarbon and a surfactant of the formulae (I) or (II) above, and then removing the composition from the article, for example by evaporation.

The invention still further provides a method for imparting soil repellency to a fabric which comprises contacting or exposing the fabric to a composition comprising effective amounts of a halocarbon and a surfactant of the formulae (I) or (II) above, and then removing the halocarbon from the fabric, for example by evaporation while depositing the surfactant on the fabric.

Methods of contacting are not critical and can vary widely. For example, the article can be immersed in a container of the composition, or the article can be sprayed using conventional equipment. Complete immersion of the article is preferred because it generally insures contact between the composition and all exposed surfaces of the article. However, any other method which can easily provide such complete contact can be used. The liquid contacting time can vary widely. Usually, the contacting time is up to about 10 minutes, however, this is not critical and longer times can be used if desired. In the preferred embodiment of the invention, the contacting time is from about 1 second to about 5 minutes, and in a particularly preferred embodiment is from about 5 seconds to about 4 minutes. Among these preferred embodiments most preferred are those embodiments in which the contacting time is from about 5 seconds to about 3 minutes.

Contacting temperatures also can vary widely depending on the boiling point of the composition. In general, the contacting temperature is equal to or less than such boiling point. After the contacting step, the article is removed from contact with the composition and removal of compositions adhering to exposed surfaces of the article is effected by evaporation by conventional means. Optionally the remaining minimal amounts of surfactant adhering to exposed surfaces of the article can be further removed by contacting the article with surfactant free solvent that is hot or cold. Finally, holding the article in the solvent vapor will further decrease the presence of surfactant residues remaining on the article. Again removal of solvent adhering to the surface of the article is effected by evaporation. In general evaporation of the composition is effected in less than about 30 seconds, and preferably less than about 10 seconds. Neither temperature nor pressure is critical. Atmospheric or subatmospheric pressures can be employed and temperatures above and below the boiling point of the halocarbon component can be used. Optionally additional surfactants may be included in the overall composition as desired by the skilled artisan. Still further, an optional cosolvent can be included. Such may include alcohols, ethers, ketones and esters, preferably those which do not extract appreciably into water. Also preferred would be a second halocarbon. When a co-solvent is employed it may be present in an amount of from about 1% to about 50% percent and more preferably from about 4% to about 45% based on the weight of the overall composition.

In a further embodiment of the invention, a substrate, such as a fabric may be provided with a coating of the above surfactant in an amount effective to provide the fabric with a soil repellant characteristic. This may be accomplished by dissolving the surfactant in a suitable solvent therefore, preferably a halocarbon such as those enumerated above, the fabric is then wetted with the composition by spraying or by immersion, the latter as in the case of a drycleaning machine, for a length of time sufficient to cause the composition to imbibe into the fabric. Such times may be the above listed contact times. The fabric is then removed from the composition and the solvent evaporated as above, thus leaving surfactant on the fabric. Moreover, the surfactant, preferably in solution in a halocarbon, can enhance the removal of soils from fabric by contacting the soiled fabric, e.g. garments, with the liquid solvent-surfactant mixture.

The composition and process of this invention are preferably used/carried out using conventional drying or drycleaning machines and systems as appropriate. Illustrative of such drying machine are those described in U.S. Pat. No. 3,386,181 which is incorporated herein by reference. The following non-limiting examples serve to illustrate the invention.

EXAMPLE 1

Preparation of dimethyl benzyl
1,1,2,2-tetrahydroperfluorodecyl amine iodide 28.7 g (0.05 mol) of $C_{10}H_4F_{17}I$, 27 g (0.2 mol) of dimethylbenzylamine and 100 ml pyridine were heated at 85°±5° C. for 6 hours. After approximately 2 hours at 80° C. a precipitate was observed in the solution. Continued heating produced additional precipitate. The light yellow solution increases in intensity and approaches red. The mixture is cooled to 20° C. and the precipitate filtered. 10.68 g of yellow platelettes are isolated. The mother liquor is allowed to stand overnight. An additional 2.04 g of solid is isolated. mp=195°–197° C. with decomposition. This example illustrates the preparation of an intermediate which is used in Example 2.

EXAMPLE 2

Synthesis of dimethylbenzyl 1,1,2,2-tetrahydroperfluorodecyl amine salt of 4-tert-octylphenyl (mono- and di-) acid phosphate To a 100 ml round bottom flask was added 3.75 g of octylphenyl acid phosphate neutralized with triethylamine. Then 72 g of CFC-113 was added and the mixture was heated to reflux. Next, 5.02 g of dimethyl benzyl 1,1,2,2-tetrahydroperfluorodecyl amine iodide from Example 1 was added to the refluxing mixture. After 2½ hours, the reaction was cooled and 25 ml of water was added. The organic layer phase was separated, diluted with an additional 250 ml of CFC-113 followed by a 100 ml water washing. The resulting organic layer was phase separated and the solvent removed under vacuum to yield 5.93 g of product.

EXAMPLE 3

Preparation of diethyl 1,1,2,2-tetrahydroperfluorodecyl amine

Into a 200 ml flask is charged 54 g of $C_8F_{17}(CH_2)_2I$, 29.2 g of $NH(C_2H_5)_2$ and 100 ml of pyridine. The mixture was heated at 80° C. for 4 hours. A two phase system resulted. The lower phase was separated from the less dense material. The lighter phase was washed with 10% NaOH solution at 50° C. to produce an additional amount of material which was added to the dense phase. The combined phases were washed with 50 ml of 10% NaOH, then 50 ml of water. The resulting organic layer was dried over $MgSO_4$ and then distilled. Fraction 1: T=40°–85° c. at 10 mm Hg yielded 6.4 g of material which was determined by nmr to be $C_8F_{17}CH=CH_2$. Fraction 2: T=85°–100° C. at 2–5 mm Hg yielded 20 g of light yellow liquid which was identified by nmr to be predominantly the product $C_8F_{17}(CH_2)_2N(C_2H_5)_2$; approximately 2% olefin $C_8F_{17}CH+CH_2$ and approximately 2% $C_8F_{17}(CH_2)_2I$. This example illustrates the preparation of an intermediate which is used in Example 4.

EXAMPLE 4

Preparation of diethylmethyl 1,1,2,2-tetrahydroperfluorodecyl amine iodide 10 g of diethyl 1,1,2,2-tetrahydroperfluorodecyl amine and 50 ml of methyl iodide (excess) were heated to approximately 40°–45° C., the reflux temperature of methyl iodide, for one hour under nitrogen. After approximately 15 minutes, a white precipitate began to form. After 4 hours at reflux, the reaction mixture was cooled to room temperature, filtered and air dried. Yield was 10.87 g of white platelettes. The remaining solvent was evaporated to yield an additional 1.61 g of light yellow solid. Both were identical by nmr. Yield 12.48 g (98%) of a material which melts at >205° c. with decomposition. This example illustrates the preparation of an intermediate which is used in Example 5.

EXAMPLE 5

Synthesis of diethylmethyl 1,1,2,2 tetrahydroperfluorodecyl amine salt of 4-tert-octyl(mono- and di-) acid phosphate To a 50 ml round bottom flask were added 4.08 g of octylphenylacid phosphate. To this was added 21.8 g of CFC-113. The mixture was heated to reflux to dissolve the octylphenylacid phosphate. Next, triethylamine was added until the acid was neutralized. An additional 20 grams of CFC-113 was added as diluent. Refluxing is continued. Finally, 5.05 g of diethylmethyl 1,1,2,2-tetrahydroperfluorodecylamine iodide was added. Refluxing continued for 2½ hours. After cooling an additional 650 ml of CFC-113 was added. The triethylamine hydroiodide by-product was removed from the product by water washing (40 ml). The organic phase which contained the product was isolated from the CFC-113 diluent by vacuum evaporation. From this, 8.6 g of product is collected.

EXAMPLE 6

Preparation of $CF_3CF_2CH_2CH_2F$

A two gallon autoclave was evacuated and charged with 12 g CuCl dissolved in 720 ml acetonitrile. The autoclave contents were cooled to –1° C. briefly evacuated again, and charged with 943 g (3.83 mol) $CF_3CF_2I$ (available from Aldrich Chemical Company). Vinyl fluoride (191.2 g, 4.22 mol available from PCR Inc.) was then added and the contents were stirred and heated to 185°–190° C. over a period of one hour. Heating was continued for 24 hours thereafter, during which time the pressure within the autoclave decreased from an original 520 psig (3584 KPa) to 295 psig (2033 KPa). Analysis of the contents indicated that 92% of the $CF_3CF_2I$ had been converted. After cooling the reaction mixture to 0° C. and venting the volatiles, a total of 1546 g of brown liquid was recovered. The crude liquid was washed with 250 ml saturated aqueous $Na_2SO_3$ followed by six water washes to remove residual acetonitrile, and finally dried ($Na_2SO_4$). Distillation provided 490 g (1.68 mol, 44% yield of pure $CF_3CF_2CH_2CHFI$ boiling between 90°–00° C. (mainly 98°–99° C.). $^1H$ NMR: delta 7.15 (ddd, 1H), 3.2 (m, 2 H); $^{19}F$ NMR: 187 (s, 3 F), –121 (m, 2 F), and –145 (m, 1 F) ppm.

A 1-liter, 3-necked flask, fitted with a –10° C. condenser (connected to –50° and 78° C. cold traps), was charged with 210 g (3.21 mol) powdered Zn. To this was added a solution of 270 ml concentrated HCl in 100 ml water. This mixture was stirred mechanically while heating to 40° C. The iodide ($CF_3CF_2CH_2CHFI$, 250 g, 0.856 mol) was then added over 1 hour through an addition funnel. The temperature was increased to 90°–100° C. over 1 hour and maintained at that temperature for an additional hour during which time the product collected in the cold traps. There was obtained 91 g of 94.4% pure $CF_3CH_2CH_2CH_2F$ (0.548 mol, 64% yield). Distillation provided pure material, b.p. 44°–45° C.

EXAMPLE 7

Evaluation of Hydrophobic Fluorinated Surfactant in Various Solvents-Drying

In order to evaluate the performance of a surfactant/solvent solution in the displacement of water from water-wet work pieces, a 'life test' is performed. In the test, 35 ml of the sample solution is placed in a 100 ml beaker fitted with a cooling coil. The solution is brought to boiling. The cooling coil confines the solvent vapor to the beaker. Duplicate 316 stainless steel coupons, wet abraded to a water-break-free condition and dried with acetone and methanol, are immersed in water and then into the boiling sample solution. The time required to displace the water from the coupon is recorded. A minimum observation time of 5.0 seconds exposure was chosen.

After an initial evaluation of drying performance, 35 ml of tap water is added to the boiling solution. The solution is kept boiling for five minutes in order to provide contact of the solution with the water. The mixture was transferred to a separatory funnel. The time for the solvent/surfactant solution and water phases to separate was noted. The time of separation, clarity of the phases, and the presence of any emulsion layer was noted. Rapid separation into clear phases with no emulsion layer is an indication that the solution will perform successfully in the application. A clear water phase indicates that no gross loss of drying solvent to the water effluent of a commercial drying machine would be expected. In this test, a clear solvent phase points to the ability of a drying solvent to expel displaced water from a drying machine in a practical time frame, i.e., water will not accumulate in the solvent phase.

The water washing was performed a total of four times with subsequent determination of drying time, that is the time required to displace water from the test coupon, after each water washing. It is known from experience with commercial drying solvents that after the life test, the final drying time should be no longer that one minute. Final drying times much in excess of one minute indicate that the bath life of the drying solvent will be inadequate in commercial application.

In Table I below, initial drying performance, phase separation behavior, and the performance as a function of water throughput are given for various solvents and surfactants.

TABLE I

| | Drying Surfactant Performance in Various Solvents | | | | | | | |
|---|---|---|---|---|---|---|---|---|
| | Initial Drying | Phase Separation | Phase Clarity | | Dry Time After Water Wash (sec) | | | |
| Solvent/Surfactant | Time, (sec) | Time, (sec) | Top | Bottom | 1st | 2nd | 3rd | 4th |
| HFC 356mcfq[1], 500 ppm Surfactant A[2] | 5 | instantaneously | Y | N | 5 | 10 | 45 | 60 |
| dichlorofluoroethane 500 ppm Surfactant A | 25 | 20 | Y | N | 10 | 15 | 20 | —[3] |
| HFC 43-10mee[4] 500 ppm Surfactant A | 5 | 45 | N | N | 5 | 15 | — | — |
| CFC-113[5], 500 ppm Surfactant DRS[6] | 5 | 10 | N | N | 5 | 5 | 10 | 10 |
| 1-H perfluoroheptane, 500 ppm Surfactant A | 5 | instantaneously | Y | N | 5 | 5 | | |
| HFC 245ea[7], 500 ppm Surfactant A | 60 | 10 | N | N | 60 | — | — | — |
| perfluoromethylcyclohexane, 500 ppm Surfactant A | surfactant insoluble | | | | | | | |
| perfluorohexane/ perfluoroheptane blend, 500 ppm Surfactant A | surfactant insoluble | | | | | | | |
| HFC356mcfq, 500 ppm Surfactant B[8] | 5 | 5 | N | N | 5 | 5 | 5 | 5 |
| HCFC-225cb[9], 500 ppm Surfactant A | 5 | | Y | N | 5 | 5 | 10 | 25 |

[1]1,1,1,2,2,4-Hexafluorobutane
[2]Surfactant A is the diethyl methyl 1,1,2,2-tetrahydroperfluorodecylamine salt of octyl phenyl acid phosphate
[3]not run
[4]1,1,1,2,2,3,4,5,5,5-decafluoropentane
[5]1,1,2-trifluoro, 1,2,2-trichloroethane
[6]DRS surfactant is a quaternary amine salt of octylphenylacid phosphate in AlliedSignal's Genesolv DRSC
[7]1,1,2,3,3-pentafluoropropane
[8]Surfactant B is dimethylbenzyl 1,1,2,2-tetrahydroperfluorodecylamine salt of octylphenyl acid phosphate
[9]1,3-dichloro-1,1,2,2,3-pentafluoropropane This example shows that the diethyl methyl 1,1,2,2-tetrahydroperfluorodecyamine salt of octylphenyl (mono- and di-) acid phosphate surfactant performs well with respect to drying time, phase separation time, phase clarity and drying time after water wash. A surfactant such as diethyl benzyl 1,1,2,2-tetrahydroperfluorodecylamine salt of octyl phenyl acid phosphate would also be expected to perform well in such and application. Variations in hydrocarbon chain length, fluorocarbon chain length, and the presence of either aromatic or aliphatic hydrocarbon chains on the amine would yield a variety of useful surfactants for water displacement. Likewise, the phosphate anion may contain either aliphatic or aromatic hydrocarbon chains. Chain length needs to be long enough to provide hydrophobicity which is key to water displacement and insolubility in water. The latter influences bath life and reflects the desire to keep the surfactant in the solvent rather than having it leave with effluent water. Surfactants subjected to the 'life test' above are selected by using a drying screening test, which is in essence the initial drying performance test as described above. In Table II below, the drying activity of various surfactants is derived from the observation of the time required for a water film to be displaced from a metal test specimen. Observation was truncated at 60 seconds.

TABLE II

Surfactant Drying Screening 1000 ppm surfactant

| Surfactant | Solvent | | |
|---|---|---|---|
| | HFC-245ea | HFC 356mcfq | perfluor-methyl-morpholine |
| 3M FC-120 (anionic) | insoluble | insoluble | not run |
| 3M FC-135 (cationic) | soluble not dry | insoluble | not run |
| 3M FC-170c (fluorinated alkylpolyoxyethylene) | soluble not dry | insoluble | not run |
| 3M FC-171 (fluorinated alkyl alkoxylate) | soluble not dry | soluble not dry | not run |
| 3M FC-431 (fluorinated aliphatic polymeric ester | soluble not dry | dry 60 sec. | not run |
| 3M FC-740 (fluorinated alkyl ester)* | insoluble | insoluble | not run |
| 3M perfluoroaliphatic amidoalkanol | dry 30 sec. | soluble not dry | dry 30 sec |
| Air Products Dabco DC193 (polyalkyl-siloxane) | not run | dry 60 sec. | not run |
| Du Pont Zonyl FSO-100 (fluorinated non-ionic polymeric ethyleneoxide) | soluble not dry | soluble not dry | not run |
| OSI Specialties, Inc. Silwet L-7500 (poly-alkylene oxide modified poly dimethylsiloxane) | not run | insoluble | not run |
| Witco Emphos CS-131 (polyoxyalkylated alkylaryl phosphate ester) | not run | insoluble | not run |
| Witco Witconol NP-15, poly(oxy-1,2-ethanediyl)alpha-(nonylphenyl)omega-hydroxy | not run | slightly soluble not dry | not run |
| DuPont Zonyl RP (telomer B phosphate diethanol amine salt | not run | insoluble | not run |
| Rhone-Poulenc Rhodaquat DAET-90 (complex ditallow quaternary sulfate | not run | insoluble | not run |
| Albright & Wilson Amgard ND (dimelamine phosphate) | not run | insoluble | not run |
| Albright & Wilson Amgard MC (ammonium poly-phosphate) | not run | insoluble | not run |
| Ethox Chemicals, Inc. CAM-2 (polyoxyethylene coconut amine) | not run | insoluble | not run |
| Tomah Products, Inc. E-S-2 (dihydroxyethyl soya amine) | not run | insoluble | not run |

*perfluoroaliphatic carboxamido or sulfonamido alkanol.

Drying solvent compositions are not limited to the use of one surfactant in one solvent. Surfactants can be used in combination. Also, certain surfactants known to be useful in water displacement, e.g., in a solvent such as chlorofluorocarbon-113, may be either insoluble or only sparingly soluble in hydrofluorocarbons. The incorporation of a co-solvent which is soluble in the hydrofluorocarbon and renders the surfactant soluble in the combined solvent matrix was found to be a useful means to employ surfactants which are essentially insoluble in hydrofluorocarbon alone. The co-solvent would preferably form an azeotrope with the hydrofluorocarbon although it is not required. However, if the co-solvent does not azeotrope, then it must be higher boiling than the hydrofluorocarbon in order to remain with the surfactant in the boiling (drying) chamber of a commercial drying machine. It is also useful to select a co-solvent which is essentially insoluble in water so that the co-solvent is not carried out of the drying machine with the effluent (displaced) water. It is realized that water-soluble co-solvents might also be used, but would have to be replenished thus creating extra maintenance.

EXAMPLE 8

The drying performance of dimethyl benzyl 1,1,2,2-tetrahydroperfluorodecylamine salt of octylphenyl(mon- and di-)acid phosphate in HFC-356mcf is illustrated in this example. The time required for the boiling formulation to displace a water film from a stainless steel coupon immersed in the mixture is noted. The minimum time chosen for immersion in the boiling mixture is five seconds. The drying performance was checked initially and then again after each of four equal volume water washes. The water washes reflect the ability of the surfactant to remain in the solvent rather than being extracted by water. Just as the brevity of the initial drying time is a desirable feature, conservation of the drying performance with continued water contact is desirable. This is an indicator of the ability of the formulation to displace process water on an on-going basis (bath life). In this example 500 ppm by weight of the dimethyl benzyl 1,1,2,2-tetrahydroperfluorodecylamine salt of octylphenyl-(mon- and di-)acid phosphate surfactant was dissolved in HFC-356mcf. Drying performance was evaluated as described above. The drying time (performance) was initially 5.0 seconds or less and did not decline to beyond 5 seconds through any of the four consecutive water washings. The drying time initially was 5.0 seconds. The drying time after each of the first through fourth wash was 5.0 seconds.

EXAMPLE 9

An example of the use of a co-solvent for the purpose of solubilizing an hydrophobic surfactant in a hydrofluorocarbon appears in Table III. Reasons for not employing the co-solvent as the sole solvent relate to issues such as toxicity, flammability, or environmental acceptability. The drying test conducted was described earlier as the initial drying performance in the 'life test'.

TABLE III

Hydrofluorocarbon Drying Solvent Employing a Co-solvent and Surfactant

| Composition | Drying time, seconds |
|---|---|
| HFC-245ea[1], 500 ppm DRS[2] | not run[3] |
| HFC-245ea, 5% wt. trichloroethylene, 500 ppm DRS | 30 |
| HFC-245ea, 5% wt. trichloroethylene 1000 ppm DRS | 10 |
| HFC-245ea, 10% wt. trichloroethylene 1000 ppm DRS | 5 |

[1]1,1,2,2,3,3-pentafluoropropane
[2]DRS is the surfactant found in Allied Signal's commercially available Genesolv DRSC Drying Solvent, a product which uses fluorocarbon -113 as the solvent.
[3]DRS was not soluble in HFC-245 ea to a level of 500 ppm.

Because the surfactant was not soluble in the hydrofluorocarbon to at least 500 ppm, the initial drying test for DRS surfactant in HFC-245ea was not performed. The 500 ppm level is considered a practical level for such systems since systems running at lower surfactant levels require frequent surfactant makeup additions. The additions compensate for surfactant which leaves the drying system adsorbed on the surface of the work that was dried.

EXAMPLE 10

Evaluation of alkyl perfluoroalkylamine salt of octylphenyl acid phosphate in drycleaning or treatment of apparel Drycleaning solvent performance may be enhanced by adding a surfactant that prevents redeposition of soil during the cleaning process. Likewise, surfactants may be added to the drycleaning solvent which impart water and/or soil repellency. Placement of a water or oil droplet on the surface of woven cotton fabric and observation of the rate of absorption can indicate the level of water or oil repellency. Hence in Table IV below, the oil repellency of diethyl methyl 1,1,2,2-tetrahydroperfluorodecylamine salt of octylphenyl acid phosphate deposited from HFC-356mcfq is illustrated.

A 2"×2" cloth swatch was first immersed in HFC solvent containing surfactant. The cloth was then removed and allowed to dry. Next, an oil droplet was deposited on the surface of the swatch. The time required for the oil droplet to absorb into the cloth swatch was noted. The lengthier times are indicative of greater oil repellency. Other hydrofluorocarbon solvents suitable for drycleaning and other surfactants such as diethyl benzyl- or diethyl phenyl 1,1,2,2-tetrahydroperfluorodecylamine salts of phosphate esters would be useful in such application.

TABLE IV

Oil Repellency of Fabric Treated with Perfluoroalkylamine Salt of Phosphate Ester

| 20W motor oil droplet | Diethyl methyl 1,1,2,2-tetrahydroperfluorodecylamine salt of octylphenyl acid phosphate concentration in HFC-356mcfq (ppm by weight) | | | |
|---|---|---|---|---|
| absorption time (seconds) | 0 | 500 | 1000 | 5000 |
| TRIAL 1 | 21 | 105 | 54 | 225 |
| TRIAL 2 | 20 | 84 | 73 | 201 |

EXAMPLE 11

In drycleaning, surfactant may be added to the drycleaning solvent in order to impart oil and/or water repellency. In this way, no subsequent treatment is required. In this example, clean 2"×2" cotton fabric swatches were analyzed for initial brightness and color using a Milton Roy ColorMate Color Analyzer, available from Milton Roy Co., Rochester, N.Y. The instrument was set to a white tile standard. The difference from the standard was reported. Next, a droplet of oil was placed on the cloth. The time required for the droplet to absorb into the cloth is noted. Then an additional nine drops of oil are deposited on the swatch. The swatches were allowed to air dry overnight (18 hours). Color and brightness readings were taken again. The soiled swatches were then placed in vials containing solvent or solvent and surfactant. The vials were shaken for 3.0 minutes and then the swatches were removed and allowed to dry. Once more, color and brightness readings were taken. Finally, an oil droplet was placed on the swatch to determine absorption time, which serves as a measure of oil repellency. Color and brightness readings as well as oil absorption times are given in Table V for HFC-356mcf with 3.9% wt. isopropanol and surfactant. The color and brightness readings of the washed swatches were in between the values measured for initial, clean swatches and the values found for the fully soiled swatches. The optimum cleaning cycle was not derived. A commercial drycleaning cycle would include multiple cleaning steps. Table VI shows the results of similar tests for a similar composition without the isopropanol co-solvent. In Tables V and VI, measurements are made according to both the Hunter Color Space evaluation system and the tristimulus coordinates. In the eye, cone receptors code light to dark, red to green, and yellow to blue signals. In the Hunter Color Space system, the letter "a" denotes redness (positive value) to greenness (negative value), the letter "b" denotes yellowness (positive value) to blueness (negative value). The lightness variable L ranges from zero for black to 100 for white. Tristimulus values X, Y and Z allow a mathematical representation of color based on the trichromacy of vision. For matching color evaluations, two stimuli produce the same color if each of the tristimulus values X, Y and Z are equal for the two respective stimuli.

TABLE V

HFC/Alcohol Solvent and Fluorinated Quaternary Amine Salt of Phosphate Ester-Cleaning and Soil Repellency

| Oil | Color/Brightness Category | Difference Reading | | | % Recovery | Oil Absorption Time | | | |
|---|---|---|---|---|---|---|---|---|---|
| | | Initial | Soiled | Cleaned | | | | | |
| Case I: with surfactant | | | | | | | | | |
| Bowman's | L | −4.83 | −35.51 | −16.16 | 63.1 | 1 min. | 24 sec. | 11 min. | 20 sec. |
| Thread | a | 0.09 | 39.30 | 15.45 | 61.0 | 1 min. | 24 sec. | | |
| Sealant | b | −1.91 | 1.86 | −2.05 | — | 1 min. | 24 sec. | | |
| | X | −8.26 | −38.28 | −19.51 | 63.6 | 1 min. | 24 sec. | | |
| | Y | −8.75 | −53.48 | −27.47 | 58.1 | 1 min. | 24 sec. | | |
| | Z | −6.47 | −57.50 | −26.21 | 61.3 | 1 min | 24 sec. | | |
| | dE | 5.19 | 53.00 | 22.45 | 64.0 | 1 min. | 24 sec. | | |
| Case II: without surfactant | | | | | | | | | |
| Bowman's | L | −4.51 | −36.83 | −18.25 | 57.5 | | | | |

TABLE V-continued

HFC/Alcohol Solvent and Fluorinated Quaternary Amine Salt of Phosphate Ester-Cleaning and Soil Repellency

| Oil | Color/Brightness Category | Difference Reading Initial | Soiled | Cleaned | % Recovery | Oil Absorption Time | |
|---|---|---|---|---|---|---|---|
| Thread | a | −0.01 | 41.33 | 18.04 | 56.3 | | |
| Sealant | b | −1.93 | 2.49 | −2.16 | — | | |
| | X | −7.77 | −39.37 | −21.64 | 56.2 | | |
| | Y | −8.19 | −54.98 | −30.64 | 52.0 | | |
| | Z | −5.84 | −59.61 | −29.46 | 56.1 | | |
| | dE | 4.90 | 55.42 | 25.76 | 58.7 | | |
| Case III: with surfactant | | | | | | | |
| Hocut 763 | L | −4.48 | −14.91 | −10.11 | 46.1 | 2.0 sec. | 5.0 sec. |
| | a | 0.04 | −7.03 | −6.27 | 10.8 | 2.0 sec. | |
| | b | −2.04 | 4.35 | 3.19 | — | 2.0 sec. | |
| | X | −7.70 | −27.24 | −19.75 | 38.3 | 2.0 sec. | |
| | Y | −8.14 | −25.52 | −17.80 | 44.4 | 2.0 sec. | |
| | Z | −5.63 | −32.18 | −22.90 | 35.0 | 2.0 sec. | |
| | dE | 4.93 | 17.05 | 12.32 | 39.0 | 2.0 sec. | |
| Case IV: without surfactant | | | | | | | |
| Hocut 763 | L | −4.49 | −14.67 | −10.55 | 40.5 | | |
| | a | 0.01 | −8.56 | −7.56 | 11.7 | | |
| | b | −1.98 | 3.19 | 1.99 | — | | |
| | X | −7.72 | −27.56 | −21.01 | 33.0 | | |
| | Y | −8.15 | −25.15 | −18.52 | 39.0 | | |
| | Z | −5.72 | −30.36 | −22.04 | −33.8 | | |
| | dE | 4.90 | 17.28 | 13.13 | 33.5 | | |

TABLE VI

HFC Solvent and Fluorinated Quarternary Amine Salt of Phosphate Ester-Cleaning

| Oil | Color/Brightness Category | Difference Reading Initial | Soiled | Cleaned | % Recovery |
|---|---|---|---|---|---|
| Case I: with surfactant) | | | | | |
| Bowman's Thread Sealant | L | −4.69 | −39.11 | −23.54 | 45.2 |
| | a | 0.01 | 43.09 | 25.93 | 39.8 |
| | b | −1.91 | 3.53 | −1.81 | — |
| | X | −8.07 | −41.73 | −26.37 | 45.6 |
| | Y | −8.51 | −57.48 | −38.26 | 39.2 |
| | Z | −6.22 | −63.01 | −38.00 | 40.3 |
| | d | 5.06 | 58.30 | 35.07 | 43.6 |
| Case II: without surfactant | | | | | |
| Bowmen's Thread Sealant | L | −4.63 | −36.83 | −23.66 | 40.9 |
| | a | 0.04 | 41.04 | 25.52 | 37.9 |
| | b | −2.06 | 2.34 | −2.47 | — |
| | X | −7.96 | −39.44 | −26.71 | 40.4 |
| | Y | −8.41 | −54.96 | −38.43 | 35.5 |
| | Z | −5.89 | −59.46 | −37.44 | 41.1 |
| | dE | 5.07 | 55.19 | 34.88 | 40.5 |
| Case III: with surfactant | | | | | |
| Hocut 763** | L | −4.55 | −14.87 | −11.46 | 33.0 |
| | a | 0.02 | −6.61 | −5.56 | 15.8 |
| | b | −1.94 | 4.96 | 3.96 | 14.5 |
| | X | −7.82 | −27.01 | −21.49 | 28.8 |
| | Y | −8.26 | −25.46 | −20.02 | 31.6 |
| | Z | −5.90 | −32.90 | −26.16 | 25.0 |
| | dE | 4.94 | 17.02 | 13.34 | 30.5 |
| Case IV without surfactant | | | | | |
| Hocut 763 | L | −4.53 | −15.53 | −13.67 | 16.9 |
| | a | 0.07 | −7.05 | −7.20 | 2.0 |
| | b | −2.10 | 5.22 | 4.77 | 6.1 |
| | X | −7.77 | −28.13 | −25.20 | 14.4 |
| | Y | −8.22 | −26.48 | −23.56 | 16.0 |
| | Z | −5.63 | −34.23 | −30.76 | 12.1 |
| | dE | 4.99 | 17.83 | 16.16 | 13.0 |

Solvent: 1,1,1,2,2,4-hexafluorobutane
Surfactant: diethyl methyl 1,1,2,2-tetrahydroperfluorodecylamine salt of octylphenyl acid phosphate, 5000 ppm (Cases I and III) and 0 ppm (Case II and IV), respectively.
*Oil available from Bowman Distribution Co. Cleveland, Ohio
**Water soluble oil available from E.H. Houton & Co., Valley Forgo, Pa.

Table V shows that the swatches which contacted surfactant during the cleaning process were as a result more resistant to oil absorption as noted by the increased oil absorption times. The percent recovery comparing soiled versus clean swatches to initial swatch condition is greater in virtually every category in the case where surfactant is present. In Table VI, the percent recovery comparing soiled versus clean swatches to initial swatch condition shows enhanced cleaning for solvent plus surfactant versus solvent alone. Again, the cleaning process was not optimized. Swatches were soiled and cleaned as previously described. Oil repellency was not measured in the latter case. In Tables V and VI, a sample of cloth changes in hue and brightness when it is dirtied and then cleaned. The percent recovery is a measure of how effective the cleaning composition was to return the sample back to its initial color value. The data show a significant improvement when the surfactant of the invention is used as compared to a cleaning composition without the surfactant.

What is claimed is:

1. A surfactant of the formulae:

$$R_3\text{—}^+N(R_2)(R_1)(\text{(CH}_2)_n R_4) \quad \text{—O—P(=O)(OR}_5)(OR_6)$$

or $$R_3\text{—}^+N(R_1)(R_2)(\text{(CH}_2)_n R_4) \quad R_7\text{—P(=O)(OH)—O—P(=O)(O}^-)(OR_7)$$

wherein $R_1$, $R_2$, $R_3$ can be the same or different and are linear or branched $C_1$ to $C_{16}$ alkyl, fluoroalkyl, alkylaryl or $$CH_2\text{—}\langle\text{phenyl}\rangle\text{—}R_8$$

where $R_8$ is hydrogen or a linear or branched $C_1$ to $C_{16}$ alkyl or fluoroalkyl group;

$R_4$ is $C_1$ to $C_{18}$ perfluoroalkyl;

n is from 1 to 4;

$R_5$, $R_6$ and $R_7$ can be the same or different and are H, linear, or branched $C_1$ to $C_{16}$ alkyl, fluoroalkyl or alkylaryl group or $$\text{—}\langle\text{phenyl}\rangle\text{—}R_9$$

where $R_9$ is linear or branched $C_1$ to $C_{16}$ alkyl or fluoroalkyl group provided not more than one of $R_5$, $R_6$ and $R_7$ is H.

2. The surfactant of claim 1 which is selected from the group consisting of the diethyl methyl 1,1,2,2-tetrahydroperfluorodecylamine salt of octylphenyl (mono)acid phosphate, the diethyl methyl 1,1,2,2-tetrahydroperfluorodecylamine salt of octylphenyl (di)acid phosphate; the dimethyl benzyl 1,1,2,2-tetrahydroperfluorodecylamine salt of octyl phenyl (mono) acid phosphate and the dimethyl benzyl 1,1,2,2-tetrahydroperfluorodecylamine salt of octyl phenyl (di) acid phosphate; the diethyl benzyl 1,1,2,2-tetrahydroperfluorodecylamine salt of octyl phenyl (mono) acid phosphate and the diethyl benzyl 1,1,2,2-tetrahydroperfluorodecylamine salt of octyl phenyl (di) acid phosphate.

3. The surfactant of claim 1 which is the diethyl methyl 1,1,2,2-tetrahydroperfluorodecylamine salt of octyl phenyl acid phosphate or the dimethyl benzyl 1,1,2,2-tetrahydroperfluorodecylamine salt of octyl phenyl acid phosphate.

4. The surfactant of claim 1 which is a diethyl methyl amine salt and wherein $R_4$ is $C_8$ to $C_{16}$.

5. The surfactant of claim 1 which is a dimethyl benzyl amine salt and wherein $R_4$ is $C_8$ to $C_{16}$.

6. A surfactant composition which comprises a mixture of a plurality of surfactants according to claim 1.

7. An article which comprises a substrate and the surfactant of claim 1 deposited on the substrate.

8. The article of claim 7 wherein the substrate comprises a fabric.

9. A composition comprising effective amounts of at least one halocarbon and at least one surfactant of the formulae:

$$R_3\text{—}^+N(R_2)(R_1)(\text{(CH}_2)_n R_4) \quad \text{—O—P(=O)(OR}_5)(OR_6)$$

or $$R_3\text{—}^+N(R_1)(R_2)(\text{(CH}_2)_n R_4) \quad R_7O\text{—P(=O)(OH)—O—P(=O)(O}^-)(OR_7)$$

wherein $R_1$, $R_2$, $R_3$ can be the same or different and are linear or branched $C_1$ to $C_{16}$ alkyl, fluoroalkyl, alkylaryl or $$CH_2\text{—}\langle\text{phenyl}\rangle\text{—}R_8$$

where $R_8$ is hydrogen or a linear or branched $C_1$ to $C_{16}$ alkyl or fluoroalkyl group;

$R_4$ is $C_1$ to $C_{18}$ perfluoroalkyl;

n is from 1 to 4;

$R_5$, $R_6$ and $R_7$ can be the same or different and are H, linear or branched $C_1$ to $C_{16}$ alkyl fluoroalkyl or alkylaryl group or $$\text{—}\langle\text{phenyl}\rangle\text{—}R_9$$

where $R_9$ is linear or branched a $C_1$ to $C_{16}$ alkyl or fluoroalkyl group provided not more than one of $R_5$, $R_6$ and $R_7$ is H; and wherein the halocarbon and surfactant are present in amounts sufficient to form an effective drying, drycleaning or soil repellency composition.

10. The composition of claim 9 wherein the surfactant is soluble in the halocarbon in an amount of at least about 50 ppm.

11. The composition of claim 9 wherein the surfactant is present in an amount of from about 50 to about 5000 ppm based on the weight of the composition.

12. The composition of claim 9 wherein the surfactant is present in an amount of from about 0.005 to about 3.0 wt. % based on the weight of the composition.

13. The composition of claim 9 wherein the surfactant is present in an amount of from about 0.01 wt % to about 1.0 wt. % based on the weight of the composition.

14. The composition of claim 9 wherein the surfactant of is a diethyl methyl amine salt and wherein $R_4$ is $C_8$ to $C_{16}$.

15. The composition of claim 9 wherein the surfactant is a dimethyl benzyl amine salt and wherein $R_4$ is $C_8$ to $C_{16}$.

16. The composition of claim 9 comprising a plurality of surfactants according to claim 1.

17. The composition of claim 9 wherein the halocarbon is selected from the group consisting of chloro and fluoro substituted alkanes.

18. The composition of claim 9 wherein the halocarbon is a hydrofluorocarbon.

19. The composition of claim 9 wherein the halocarbon is selected from the group consisting of dichlorofluoroethane;

1,1,1,2,2,3,4,5,5,5-decafluoropentane; 1,1,2-trifluoro, 1,2,2-trichloroethane; 1,1,2,3,3-pentafluoropropane; 1,3-dichloro-1,1,2,2,3-pentafluoropropane and 1,1,1,2,2,4-hexafluorobutane.

20. The composition of claim 9 wherein the halocarbon is 1,1,1,2,2,4-hexafluorobutane.

21. The composition of claim 9 wherein the halocarbon is 1,1,1,2,2,4-hexafluorobutane and the surfactant is the diethyl methyl 1,1,2,2-tetrahydroperfluorodecylamine salt of octyl phenyl acid phosphate.

22. The composition of claim 9 wherein the halocarbon is 1,1,1,2,2,4-hexafluorobutane, the surfactant is a diethyl methyl amine salt and $R_4$ is $C_8$ to $C_{16}$.

23. The composition of claim 9 further comprising at least one co-solvent.

24. The composition of claim 9 further comprising at least one cosolvent selected from the group consisting of alcohols, ketones, ethers and esters.

25. The composition of claim 9 further comprising at least one cosolvent selected from the group consisting of trichloroethylene and isopropanol.

26. The composition of claim 9 further comprising at least one co-solvent in an amount of from about 4 to about 45 percent based on the weight of the overall composition.

27. The composition of claim 9 wherein the surfactant is selected from the group consisting of the diethyl methyl 1,1,2,2-tetrahydroperfluorodecylamine salt of octylphenyl (mono)acid phosphate, the diethyl methyl 1,1,2,2-tetrahydroperfluorodecylamine salt of octylphenyl (di)acid phosphate; the dimethyl benzyl 1,1,2,2-tetrahydroperfluorodecylamine salt of octyl phenyl (mono) acid phosphate and the dimethyl benzyl 1,1,2,2-tetrahydroperfluorodecylamine salt of octyl phenyl (di) acid phosphate; the diethyl benzyl 1,1,2,2-tetrahydroperfluorodecylamine salt of octyl phenyl (mono) acid phosphate and the diethyl benzyl 1,1,2,2-tetrahydroperfluorodecylamine salt of octyl phenyl (di) acid phosphate.

* * * * *